United States Patent [19]

Horie et al.

[11] Patent Number: 4,476,208

[45] Date of Patent: Oct. 9, 1984

[54] COMPOUNDS HAVING BARBITURIC ACID OR THIOBARBITURIC ACID RESIDUE, PHOTOCONDUCTIVE COMPOSITIONS AND ELECTROPHOTOGRAPHIC LIGHT SENSITIVE MATERIALS CONTAINING THE COMPOUNDS AS CHARGE GENERATING MATERIALS

[75] Inventors: Seiji Horie; Junji Nakano; Hideo Sato, all of Saitama, Japan

[73] Assignee: Fuji Photo Film Co., Ltd., Kanagawa, Japan

[21] Appl. No.: 452,654

[22] Filed: Dec. 23, 1982

[30] Foreign Application Priority Data

Dec. 23, 1981 [JP] Japan ............................. 56-207246

[51] Int. Cl.$^3$ ............................................. G03G 5/06
[52] U.S. Cl. ..................................... 430/58; 430/78; 430/900
[58] Field of Search .................. 430/81, 83, 900, 58, 430/78

[56] References Cited

U.S. PATENT DOCUMENTS 4,322,487 3/1982 Merrill et al. ..................... 430/37
4,389,477 6/1983 Kondo et al. ..................... 430/83

Primary Examiner—John E. Kittle
Assistant Examiner—John L. Goodrow
Attorney, Agent, or Firm—Sughrue, Mion, Zinn, Macpeak & Seas

[57] ABSTRACT

Novel compounds are disclosed which are composed of a barbituric acid residue or a thiobarbituric acid residue and a pyrylium salt residue, thiopyrylium salt residue, benzopyrylium salt residue, or a benzothiopyrylium salt residue. The compounds are suitable as charge generating materials for an electrophotographic light-sensitive material of the type containing a charge generating material and a charge transporting material in one layer or two separate layers. The use of the compounds improves the durability and light-sensitivity of the light-sensitive material.

11 Claims, 3 Drawing Figures

COMPOUNDS HAVING BARBITURIC ACID OR THIOBARBITURIC ACID RESIDUE, PHOTOCONDUCTIVE COMPOSITIONS AND ELECTROPHOTOGRAPHIC LIGHT SENSITIVE MATERIALS CONTAINING THE COMPOUNDS AS CHARGE GENERATING MATERIALS

FIELD OF THE INVENTION

This invention relates to novel compounds having a barbituric acid residue or a thiobarbituric acid residue and photoconductive compositions and electrophotographic light-sensitive materials containing the compounds. Furthermore, the invention relates to an electrophotographic light-sensitive material containing a charge generating material and a charge transporting material and more particularly, the invention relates to an electrophotographic light-sensitive material containing a compound having a specific barbituric acid residue or thiobarbituric acid residue as a charge generating material in a light-sensitive layer formed on a conductive support.

BACKGROUND OF THE INVENTION

A photoconductive steps carried out by an electrophotographic light-sensitive material are comprised of:
(1) generating a charge by light exposure; and
(2) transporting the charge.

As an example of performing steps (1) and (2) with the same material, there is illustrated a selenium light-sensitive plate. On the other hand, as an example of performing steps (1) and (2) with different materials, there is the well-known combination of amorphous selenium and poly-N-vinylcarbazole. The process of performing the steps (1) and (2) by different or separate materials is disirable because the range of selecting materials used for the light-sensitive materials can be enlarged, thereby the electrophotographic characteristics of the light-sensitive materials, such as sensitivity, allowable electric potential, etc., are improved, and also materials suitable for forming coated layers of the light-sensitive materials can be selected over a wide range.

Hitherto, inorganic materials such as selenium, cadmium sulfide, zinc oxide, etc., have been used as the materials for photoconductive materials of light-sensitive materials used in an electrophotographic system.

As disclosed by Carlson in U.S. Pat. No. 2,297,691, in an electrophotographic process a photoconductive material comprising a support coated with a material which is insulating in the dark but changes its electric resistance according to the exposure amount irradiated during image exposure is used. The photoconductive material is generally subjected to a dark adaptation for a proper period of time and then the surface thereof is first uniformly charged in the dark. Then, the material is image-exposed by irradiation patterns having an effect of reducing the surface charge according to the corresponding energy contained in various portions of the irradiated patterns. The surface charge or an electrostatic latent image thus remaining on the surface of the photoconductive material layer (light-sensitive layer) is brought into contact with a proper developer, i.e., a toner to provide a visible image. The toner which is contained in a insulating liquid or in a dry carrier can be attached to the surface of the light-sensitive layer in conformity to the charge patterns. The toner thus attached can be fixed by a known means such as heat, pressure, solvent vapor, etc. Also, the lectrostatic latent image can be transferred onto a 2nd support (e.g., a paper, a film, etc.,) and the electrostatic latent image thus tranferred onto the 2nd support can be developed there by the same manner as above. The electrophotographic process is one of the image-forming processes for forming images by such a manner.

The fundamental characteristics required for the light-sensitive material in such an electrophotographic process are (1) it can be charged at a proper potential in the dark, (2) the charge on the surface of it is reluctant to dissipate in the dark, and (3) the charge can be quickly dissipated by the irradiation of light. It is true that the foregoing inorganic materials conventionally used have many merits and at the same time various demerits. For example, selenium which is widely used at present sufficiently meets the foregoing factors (1)-(3) but is not desirable because the conditions for producing selenium layer are troublesome which causes an increase in the production cost thereof, it is difficult to form a belt-like light-sensitive material composed of selenium since it has no plasticity, and it must be handled carefully since it is sensitive to heat and mechanical impact. Cadmium sulfide and zinc oxide are used as a light-sensitive material in a form of a dispersion in a binder of a resin. However, such a photoconductive layer has physical faults with respect to its smoothness, hardness, tensile strength, abrasion resistance. Accordingly, it cannot be repeatedly used.

Recently, in order to eliminate the faults of the inorganic materials, electrophotographic light-sensitive materials using various organic materials have been proposed and practically used. For example, there have been proposed a light-sensitive material composed of poly-N-vinylcarbazole and 2,4,7-trinitrofluoren-9-one (see, e.g., U.S. Pat. No. 3,484,237), a light-sensitive material composed of poly-N-vinylcarbazole sensitized by a pyrylium salt series dye (see, e.g., U.S. Pat. No. 3,617,268), a light-sensitive material mainly composed of an organic pigment (see, e.g., U.S. Pat. No. 3,898,084), and a light-sensitive material mainly composed of an eutectic complex of a dye and a resin (see, e.g., U.S. Pat. Nos. 3,732,180 and 3,684,502). These light-sensitive materials have excellent characteristics and are considered to have high practical value. However, it is necessary to consider various requirements for the light-sensitive materials such as: the simplicity of the production process, the electrophotographic characteristics, and the wave length selectivity (required when applying the electrophotographic light-sensitive materials to a laser beam printer or an indication element). Materials sufficiently meeting these requirements have not yet been obtained at present.

SUMMARY OF THE INVENTION

The present inventor have investigated charge generating materials, and as a result have discovered that the novel compounds shown by general formulae (I)-(IV) as described below, which is formed by combining a barbituric acid residue or a thiobarbituric acid residue (hereinafter, they are referred to as (thio)barbutric acid residues) with a pyrylium salt residue, a thiopyrylium salt residue, benzopyrylium salt residue or a benzothiopyrylium salt residue has a good resistibility to light, heat, or air oxidation. Hence, those compounds have good stability, and are excellent as a charge generating materials, and sufficiently meet various requirements for light-sensitive materials.

It has also been found that since the compounds having the (thio)barbituric acid residues exhibit excellent charge generating function, the electrophotographic light-sensitive materials using these compounds as the charge generating materials together with charge transporting materials in combinations show very high-sensitivity, can be produced easily, have excellent durability, and have sufficient electrophotographic characteristics.

Furthermore, it has been found that the compounds having the (thio)barbituric acid residues have good wave length selectivity required when applying the electrophotographic light-sensitive materials to a laser beam printer or an indication element and also the compounds having the (thio)barbituric acid residues can be uniformly dispersed with charge transporting materials and the compounds have a property of providing light-sensitive materials having a high transparency in this case.

That is, according to the 1st embodiment of this invention, there is provided a compound having a barbituric acid residue or a thiobarbituric acid residue represented by the following general formulae (I) or (IV);

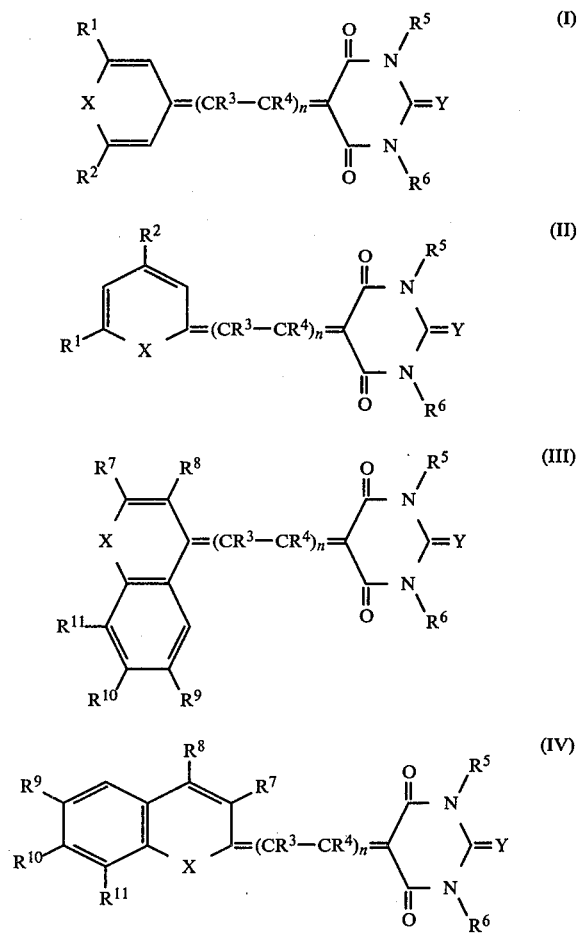

wherein;

(i) n represents 0, 1, or 2;

(ii) X and Y, which may be the same or different, each represents an oxygen atom or a sulfur atom, (iii) $R^1$ and $R^2$, which may be the same or different, each represents a hydrogen atom, an alkyl group having 1-4 carbon atoms, or a phenyl group, these groups may be substituted, (iv) $R^3$ and $R^4$, which may be the same or different, each represents a hydrogen atom, an alkyl group, an aralkyl group, or an aryl group, (v) $R^5$ and $R^6$, which may be the same or different, each represents a hydrogen atom, an alkyl group, an aralkyl group, or a phenyl group; these groups may be substituted, (vi) $R^7$ and $R^8$, which may be the same or different, each represents a hydrogen atom, an alkyl group having 1-4 carbon atoms, an unsubstituted or substituted phenyl group, or an unsubstituted or substituted naphthyl group, and (vii) $R^9$, $R^{10}$ and $R^{11}$, which may be the same or different, each represents a hydrogen atom, an alkyl group having 1-4 carbon atoms, a hydroxy group, an alkoxy group having 1-2 carbon atoms, an unsubstituted or substituted phenyl group, a nitro group, or a halogen atom.

According to the 2nd embodiment of this invention, there is provided a photoconductive composition containing the compound having a barbituric acid residue or a thiobarbituric acid residue represented by the general formulae (I) to (IV) as shown above.

According to the 3rd embodiment of this invention, there is provided an electrophotographic light-sensitive material having an electrophotographic light-sensitive layer containing a charge generating material and a charge transporting material characterized in that said charge generating material is composed of the compound having a barbituric acid residue or a thiobarbituric acid residue represented by the general formulae (I) to (IV) as shown above.

BRIEF DESCRIPTION OF THE DRAWINGS

FIG. 1 is a schematic sectional view showing an embodiment of the electrophotographic light-sensitive material of this invention, FIG. 2 is a schematic sectional view showing another embodiment of the electrophotographic light-sensitive material of this invention, and FIG. 3 is a schematic sectional view showing another embodiment of the electrophotographic light-sensitive material of this invention.

DESCRIPTION OF THE PREFERRED EMBODIMENT

The compounds represented by general formulae (I)-(IV) are explained in detail below.

In the general formulae, $R^1$ and $R^2$ represent a hydrogen atom, an alkyl group having 1-4 carbon atoms, a phenyl group; and the alkyl group and phenyl group may have a substituent. Examples of the alkyl group are a methyl group an ethyl group, a propyl group, a butyl group, a t-butyl group. Practical examples of the substituent for the substituted alkyl group are an alkoxy group having 1-4 carbon atoms, such as a methoxy group, an ethoxy group, a butoxy group, etc. Also, practical examples of the substituent for the substituted phenyl group are a halogen atom such as chlorine atom, bromine atom, etc.; a cyano group; a nitro group; an alkyl group having 1-4 carbon atoms, such as a methyl group, an ethyl group, a butyl group, etc.; and an alkoxy group having 1-4 carbon atoms, such as a methoxy group, an ethoxy group, a butoxy group, etc.

Practical examples of $R^3$ and $R^4$ are a hydrogen atom; an alkyl group having 1-12 carbon atoms, such as a methyl group, an ethyl group, a butyl group, an octyl group, etc.; an aralkyl group having 7-10 carbon atoms, such as a benzyl group, a phenethyl group, etc., and an aryl group having 6-14 carbon atoms, such as a phenyl group, a naphthyl group, etc.

Practical examples of $R^5$ and $R^6$ are a hydrogen atom; an alkyl group having 1-12 carbon atoms, such as a methyl group, an ethyl group, a butyl group, an octyl group, etc.; an aralkyl group having 7-14 carbon atoms, such as a benzyl group, a phenethyl group, etc.; and a phenyl group. These groups may be substituted and examples of the substituent include (a) an alkyl group having 1-4 carbon atoms, (b) an alkoxy group having 1-4 carbon atoms, (c) an aryloxy group having 6-7 carbon atoms, (d) an acyl group having 2-8 carbon atoms, (e) an alkoxycarbonyl group having 2-5 carbon atoms, (f) a halogen atom, (g) a monoalkyl amino group substituted by an alkyl group having 1-4 carbon atoms, (h) a dialkylamino group substituted by an alkyl group having 1-4 carbon atoms, (i) an amido group having 2-4 carbon atoms, and (j) a nitro group.

Furthermore, practical examples of the foregoing substituents are (a) a methyl group, an ethyl group, a butyl group, etc., as an alkyl group having 1-4 carbon atoms; (b) a methoxy group, an ethoxy group, a propoxy group, a butoxy group, etc., as an alkoxy group having 1-4 carbon atoms; (c) a phenoxy group, an o-, m-, or p-tolyloxy group, etc., as an aryloxy group; (d) an acetyl group, a propionyl group, a benzoyl group, or an o-, m-, or p-toluoyl group as an acyl group; (e) a methoxycarbonyl group, an ethoxycarbonyl group, a propoxycarbonyl group, a butoxycarbonyl group, etc., as an alkoxycarbonyl group having 2-5 carbon atoms; (f) a chlorine atom, a bromine atom, a fluorine atom, etc., a halogen atom; (g) a methylamino group, an ethylamino group, a butylamino group, etc., as a monoalkylamino group substituted by an alkyl group having 1-4 carbon atoms; (h) a dimethylamino group, a diethylamino group, a diporpylamino group, a dibutylamino group, an N-methyl-N-ethylamino group, etc., as a dialkylamino group substituted by an alkyl group having 1-4 carbon atoms; (i) an acetamido group, a propionamido group, etc., as an amido group, and (j) a nitro group and a phenyl group as other substituent.

Practical examples of $R^7$ and $R^8$ are a hydrogen atom; an alkyl group having 1-4 carbon atoms, such as a methyl group, an ethyl group, a butyl group, etc.; a phenyl group; a naphthyl group; and a substituted phenyl group; and practical examples of the substituted phenyl group are same as the practical examples (a)-(j) stated as to the substituents for the groups shown by $R^5$ and $R^6$.

Practical examples of $R^9$, $R^{10}$, and $R^{11}$ are a hydrogen atom; an alkyl group having 1-4 carbon atoms, such as a methyl group, an ethyl group, a butyl group, etc.; a hydroxy group; an alkoxy group having 1-4 carbon atoms, such as a methoxy group, an ethoxy group, a butoxy group, etc.; a phenyl group; a nitro group; a halogen atom such as a chlorine atom, a bromine atom, etc.; and a substituted phenyl group; and practical examples of the substituted phenyl group are same as the substituents for the substituted phenyl group in $R^1$ and $R^2$.

Practical examples of the compounds having (thio)-barbituric acid residues shown by general formulae (I)-(IV) are illustrated below, wherein, Et stands for $C_2H_5-$ (ethyl group).

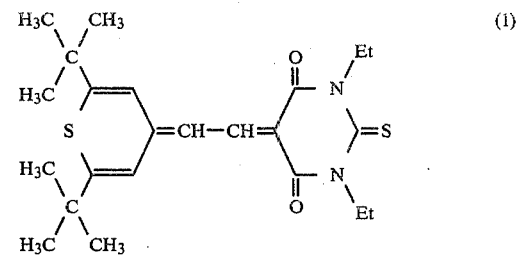

(1)

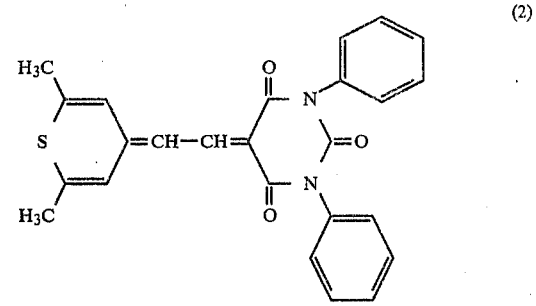

(2)

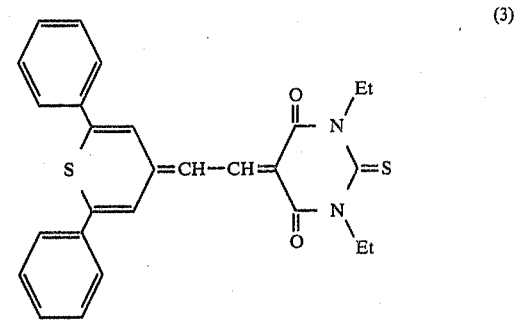

(3)

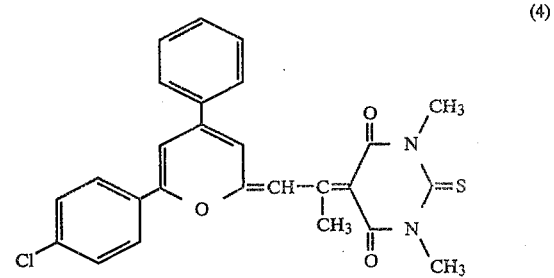

(4)

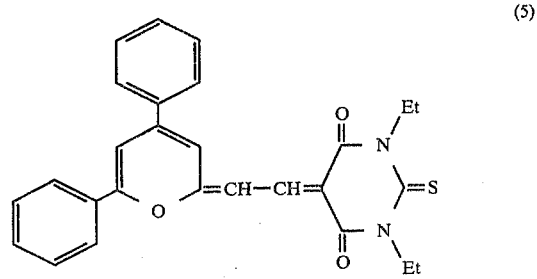

(5)

-continued
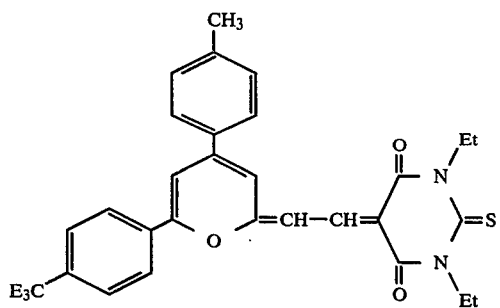 (6)
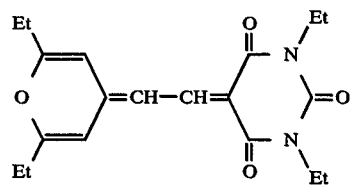 (7)
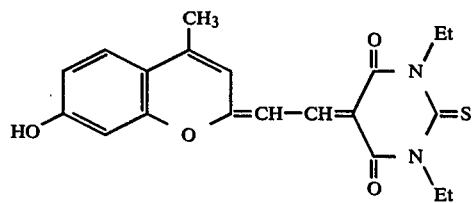 (8)
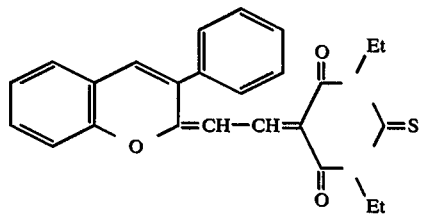 (9)
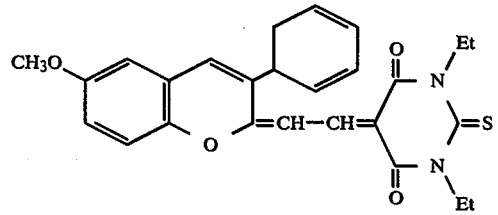 (10)
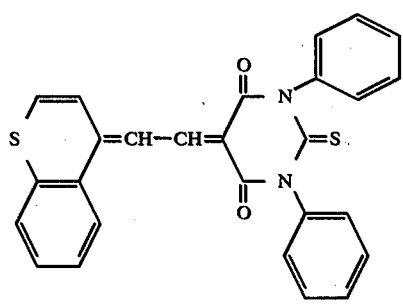 (11)
-continued
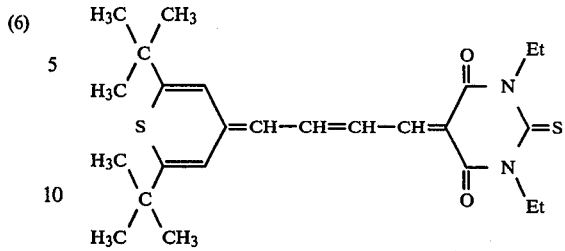 (12)
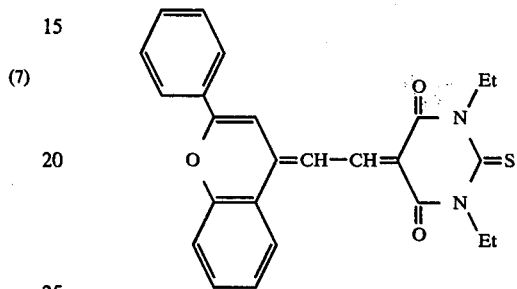 (13)
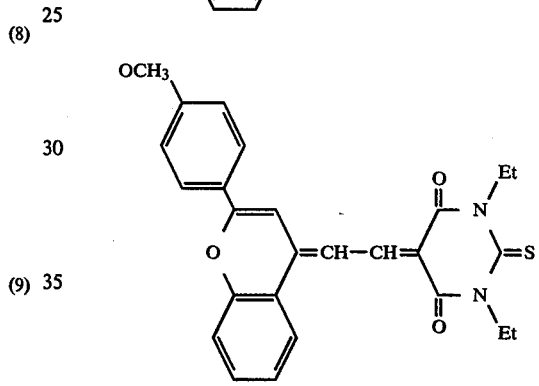 (14)
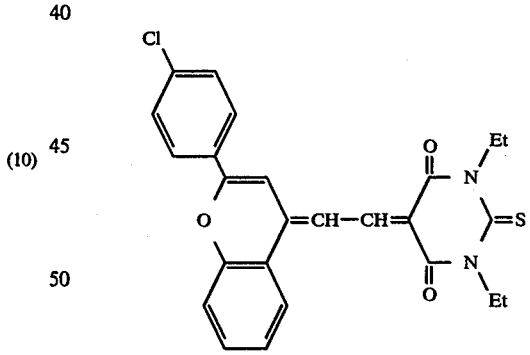 (15)
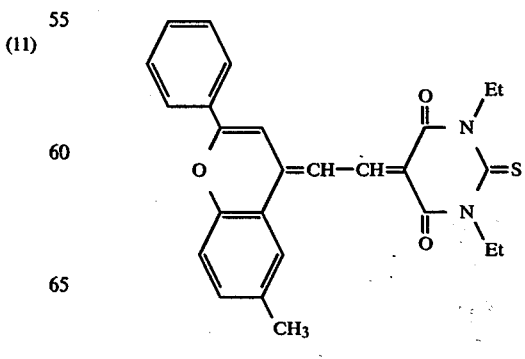 (16)

-continued
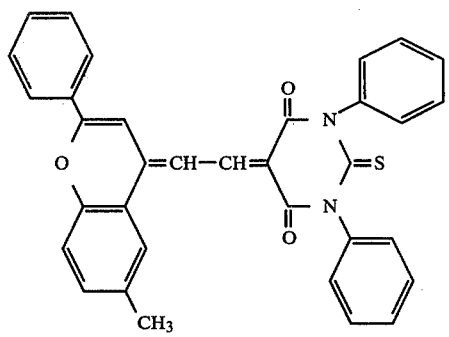 (17)
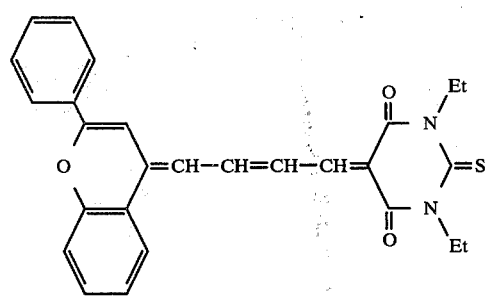 (18)
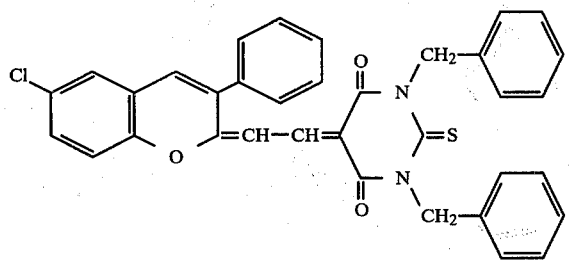 (19)
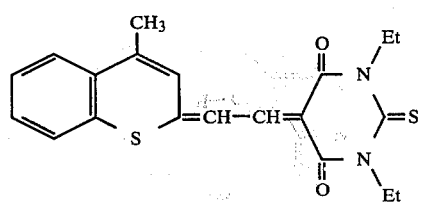 (20)
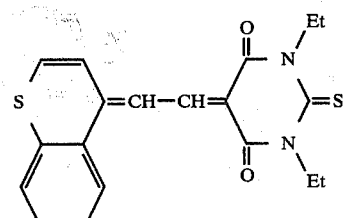 (21)
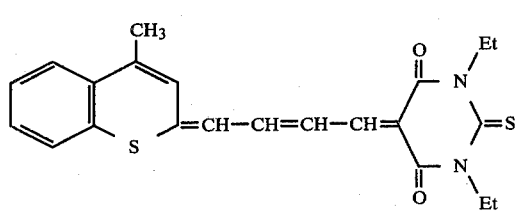 (22)
-continued
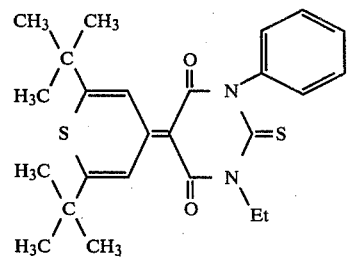 (23)
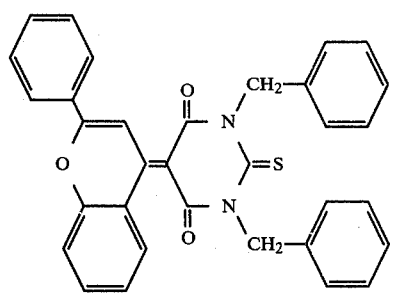 (24)
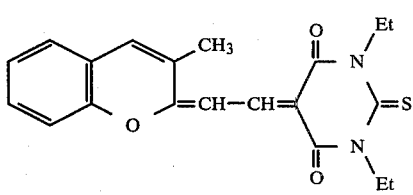 (25)
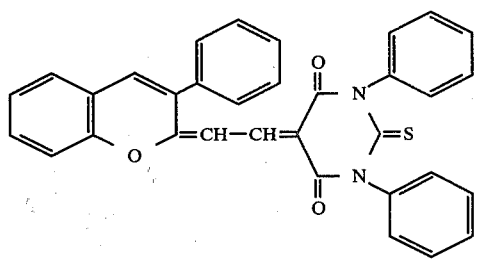 (26)
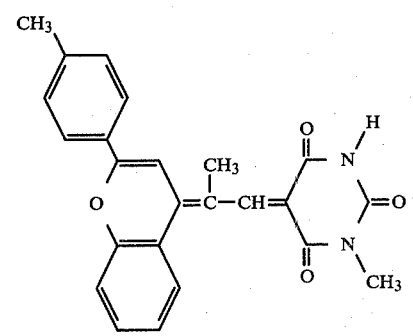 (27)
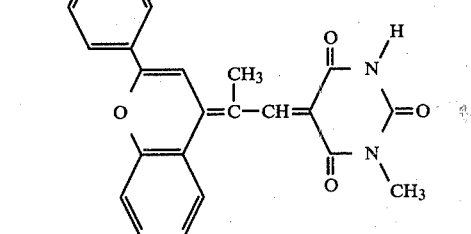 (28)

-continued

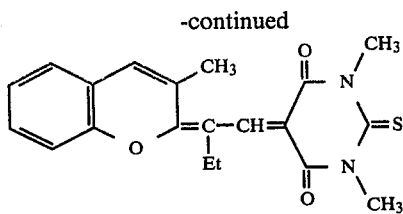 (29)

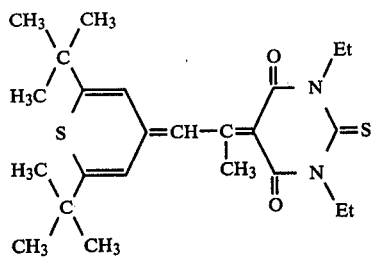 (30)

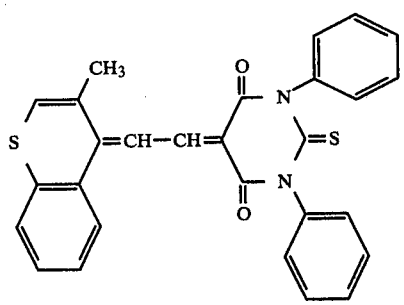 (31)

The compounds having (thio)barbituric acid residues shown by foregoing general formulae (I)–(IV) can be prepared based on the methods described in Japanese Patent Application Nos. 97,996/'71 and 4734/'71, and U.S. Pat. Nos. 2,036,546; 2,089,729; 2,165,338; 2,170,803; 263,757, 2,170,807; and 2,263,752.

That is, they can be prepared by reacting β-acetanilidovinyl derivatives (n=1) or 4-acetanilido-1,3-butadienyl derivatives (n=2) of (thio)pyrylium salt or benzo(thio)pyrylium salt and (thio)barbituric acid residues in the presence of a basic catalyst.

Productions methods typical compounds of this invention are described below.

(i) 1,3-Diethyl-2-thio-5-[(2,6-diphenyl-4-thiopyrylidene)ethylidene]barbituric acid (Compound (3)):

In 10 ml of acetic anhydride, 3 g of 2,6-diphenyl-4-methylthiopyrylium perchlorate prepared by the method described in E, Molemaar and J. Straiting, "Tetrahedron Letter", 2941 (1965) was reacted with 5 g of N,N'-diphenylformamidine for 10 minutes at 120° C. After removing the solvent, the residue was washed with ether to provide 2.3 g of the brown solid of a β-acetanilidovinyl derivative. The product was dissolved in 60 ml of acetone and then 30 ml of an alcohol solution of 0.92 g of 1,3-diethyl-2-thiobarbituric acid and 5 ml of pyridine were added to the solution. After refluxing the mixture for 20 minutes, grayish green crystals thus precipitated were recovered by filtration, washed with acetone, and then recrystallized from benzene. Thus, 1.8 g of grayish green crystals having a melting point of 314°–316° C. were obtained.

Elementary analysis for $C_{27}H_{24}N_2O_2S_2$:

|  | C (%) | H (%) | N (%) |
|---|---|---|---|
| Calculated | 68.62 | 5.12 | 5.93 |
| Found | 68.59 | 5.33 | 6.07 |

The maximum absorption wave length $\lambda_{max}$ thereof in dichloroethane was 612 n.m. and 566 n.m. and log ε of the molecular absorption coefficient ε was 4.89 and 4.77.

(ii) 1,3-Diethyl-2-thio-5-[(2,6-di-t-butyl-4-thiopyrylidene)ethylidene]barbituric acid—(Compound (1)):

By performing the reaction and the post treatment under the same conditions as in Production (i) described above using 3 g of 2,6-di-t-butyl-4-methylthiopyrylium perchlorate prepared by the method described in Japanese Patent Publication (OPI) No. 129,283/'80, 5 g of N,N'-diphenylformamidine, and 10 ml of acetic anhydride, 2.7 g of a β-acetoanilidovinyl derivative was obtained.

Green crystals were obtained by performing the reaction and post treatment as in Production (i) using the product thus obtained and 1.15 g of 1,3-diethyl-2-thiobarbituric acid and recrystallized from an alcohol.

Thus, 0.95 g of the green crystals having a melting point of 279.3°–280.7° C. were obtained.

Elementary analysis for $C_{23}H_{32}N_2S_2O_2$:

|  | C (%) | H (%) | N (%) |
|---|---|---|---|
| Calculated | 63.85 | 7.46 | 6.47 |
| Found | 64.01 | 7.43 | 6.40 |

The maximum absorption wave length $\lambda_{max}$ was 581 n.m. and log ε was 5.16.

(iii) 1,3-Diethyl-2-thio-5-[(2,4-diphenyl-6-pyrylidene)ethylidene]barbituric acid—(Compound (5)):

By following the same reaction and post treatment as in Production (i) except that 3 g of 2,4-diphenyl-6-methyl-pyrylium perchlorate prepared by the method described in U.S. Pat. No. 3,250,615 and 1.73 g of 1,3-diethyl-2-thiobarbituric acid, 2.0 g of green acicular crystals were obtained. Melting point thereof was 306.8°–307.5° C. Elementary analysis for $C_{27}H_{24}N_2SO_3$:

|  | C (%) | H (%) | N (%) |
|---|---|---|---|
| Calculated | 71.03 | 5.30 | 6.14 |
| Found | 71.29 | 5.25 | 5.96 |

The maximum absorption wave length $\lambda_{max}$ in dichloroethane was 615 n.m. and 570 n.m. and log ε was 4.60 and 4.55.

(iv) 1,3-Diethyl-2-thio-5-[(2,4di-p-tolyl-6-pyrylidene)ethylidene]barbituric acid—(Compound (6)):

By following the same reaction and post treatment as in Production (i) except that 3 g of 2,4-di-p-tolyl-6-methylpyrylium perchlorate prepared by the method described in Japanese Patent Publication No. 28,499/'65 and 2.1 g of 1,3-diethyl-2-thiobarbituric acid were used, 2.2 g of green crystals were obtained. The melting point was 293.5°–294° C.

Elementary analysis for $C_{29}H_{28}N_2SO_3$:

|  | C (%) | H (%) | N (%) |
|---|---|---|---|
| Calculated | 71.88 | 5.82 | 5.78 |
| Found | 71.70 | 5.92 | 5.77 |

The maximum absorption wave length $\lambda_{max}$ in dichloroethane was 661 n. m. and 572 n. m. and log $\epsilon$ was 4.64 and 4.56.

(v) 1,3-diethyl-2-thio-5-[(4H-flaven-4-ylidene)ethylidene]barbituric acid—(Compound (13)):

In 5 ml of acetic anhydride, 1 g of 4-methylflavylium perchlorate prepared by the method described in G. A. Reynolds et al; "J. Heterocyclic chemistry"; 7 (6), 1395(1970) was reacted with 3 g of N,N'-diphenylformamidine for 5 minutes at 120° C. The reaction mixture was cooled and the green solids thus precipitated were washed with acetone and the solvent was distilled off under reduced pressure from the red washings. The residue thus formed was washed with ether to provide 1.0 g of the red solid of β-acetanilidovinyl derivative. The product was dissolved in 60 ml of acetone and to the solution were added 20 ml of an alcohol solution of 0.46 g of 1,3-diethyl-2-thiobarbituric acid and 5 ml of pyridine. After refluxing the mixture for 20 minutes, the red-purple solids thus precipitated were recovered by filtration and washed with alcohol. Then, by recrystallizing from benzene, 0.30 g of red-purple acicular crystals having a melting point of 305°–307° C. were obtained.

Elementary analysis for $C_{25}H_{22}N_2O_3S$:

|  | C (%) | H (%) | N (%) |
|---|---|---|---|
| Calculated | 69.75 | 5.15 | 6.51 |
| Found | 69.68 | 5.11 | 6.60 |

The maximum absorption wave length $\lambda_{max}$ in dichloroethane was 581 n. m. and 538 n. m. and log $\epsilon$ was 4.78 and 4.77.

(vi) 1,3-Diethyl-2-thio-5-[(4'-methoxy-4-H-flaven-4-ylidene)ethylidene]barbituric acid—(Compound (14)):

By following the same reaction and post treatment as in Production (v) except that 1 g of 4'-methoxy-4-methylflavylium perchlorate and 0.31 g of 1,3-diethyl-2-thiobarbituric acid were used, 0.50 g of red-purple crystals were obtained.

The melting point was 309°–310° C.

Elementary analysis for $C_{26}H_{24}N_2O_4S$:

|  | C (%) | H (%) | N (%) |
|---|---|---|---|
| Calculated | 67.81 | 5.25 | 6.08 |
| Found | 67.63 | 5.36 | 6.05 |

The maximum absorption wave length $\lambda_{max}$ was 591 n. m. and 545 n. m. and log $\epsilon$ was 4.87 and 4.78.

(vii) 1,3-Diethyl-2-thio-5-[(4H-flaven-4-ylidene)-2-butenylidene]barbituric acid—(Compound (18)):

In 50 ml of benzene were dissolved 0.85 g of a 3-acetoanilidoallylidene derivative obtained by reacting propenedianyl and 1,3-diethyl-2-thiobarbituric acid in acetic anhydride and 0.74 g of 4-methylflavylium perchlorate and 5 ml of pyridine was added to the solution.

After refluxing the mixture for one hour, the solids thus precipitated were recrystallized from benzene to provide 0.50 g of green crystals having a melting point of 266.5°–267.5° C.

Elementary analysis for $C_{27}H_{24}N_2O_3S$:

|  | C (%) | H (%) | N (%) |
|---|---|---|---|
| Calculated | 71.03 | 5.30 | 6.14 |
| Found | 71.28 | 5.22 | 6.17 |

The maximum absorption wave length $\lambda_{max}$ was 609 n. m. and log $\epsilon$ was 4.82.

In the light-sensitive material of this invention, the compound having the (thio)barbituric acid residue as described above is used as a charge generating material and also used together with a charge transporting material in combination. In this case, the foregoing compound can be used as shown in FIG. 1 to FIG. 3 of the accompanying drawings.

The light-sensitive material shown in FIG. 1 is composed of a conductive support 1 at least the surface of which is conductive having formed thereon an electrophotographic light-sensitive layer 2 containing the compound 3 having a (thio)barbituric acid residue as a charge generating material dispersed in a charge transferring medium composed of a charge transporting material and a binder.

The light-sensitive material shown in FIG. 2 is composed of a conductive support 1 at least the surface of which is conductive having formed thereon a charge generating layer 5 mainly composed of the compound 3 having a (thio)barbituric acid residue and a charge transferring layer 4 containing a charge transporting material as an electrophotographic light-sensitive layer 2.

The light-sensitive material shown in FIG. 3 is composed of a conductive support 1 at least the surface of which is conductive having formed thereon a charge transferring layer 4 containing a charge transporting material and a charge generating layer mainly composed of the compound 3 having a (thio)barbituric acid residue 4 as an electrophotographic light-sensitive layer 2.

The light-sensitive material of FIG. 1 is prepared by dissolving or dispersing the compound having a (thio)barbituric acid residue in a solution containing a charge transporting material and a binder and coating the solution or the dispersion on a conductive support followed by drying.

The light-sensitive material of FIG. 2 is prepared by vacuum vapor-depositing the compound having a (thio)barbituric acid residue, which is a charge generating material, on a conductive support or coating a solution or dispersion obtained by dissolving or dispersing the compound having a (thio)barbituric acid residue in a proper solvent, if necessary, containing a binder on a conductive support followed by drying and after, if necessary, surface-finishing or adjusting the thickness of the layer by, for example, buff-polishing, coating a solution containing a charge transporting material and a binder followed by drying. Coating is performed by an ordinary means such as a doctor blade coating, wire bar coating, etc.

The light-sensitive material of FIG. 3 is prepared by coating a solution containing a charge transporting material and a binder on a conductive support by an ordinary means followed by drying and then forming a charge generating layer by the same manner as when preparing the light-sensitive material of FIG. 2.

The thickness of the light-sensitive layer is 3–50 μm, preferably 5–20 μm in the light-sensitive material of FIG. 1. Also, the thickness of the charge generating layer of the light-sensitive material shown in FIG. 2 or FIG. 3 is less than 5 μm, preferably less than 2 μm and the thickness of the charge transferring layer is 3-50 μm, preferably 5-20 μm.

The proportion of the charge transporting material in the light-sensitive layer of the light-sensitive material shown in FIG. 1 is 10-150% by weight, preferably 30-100% by weight based on the amount of the binder and the proportion of the compound having a (thio)barbituric acid residue is 1-150% by weight, preferably 5-50% by weight based on the amount of the binder.

The proportion of the charge transporting material in the charge transferring layer of the light-sensitive materials shown in FIG. 2 and FIG. 3 is 10-150% by weight, preferably 30-100% by weight as in the case of the light-sensitive layer of the light-sensitive material shown in FIG. 1. In the light-sensitive materials shown in FIG. 2 and FIG. 3, a charge generating material can be contained in a binder and in this case the proportion of the charge generating material is 1-150% by weight, preferably 5-50% by weight based on the amount of the binder. In addition, in all light-sensitive materials shown in FIGS. 1-3, a plasticizer may be used together with a binder.

In the light-sensitive materials of this invention, as the conductive support at least the surface of which has a conductive property, a metal plate or foil such as aluminum, a plastic film vapor-deposited with a metal such as aluminum, or a paper subjected to a conductive treatment is used.

The binders used in this invention include condensed resins such as polyamide, polyurethane, polyester, epoxy resin, polyketone, polycarbonate, etc., and vinyl copolymers such as polyvinyl ketone, polystyrene, poly-N-vinylcarbazole and polyacrylamide. It is also possible to use resins having an insulating property and adhesive property in this invention.

Examples of the plasticizer used in this invention include biphenyl, biphenyl chloride, o-terphenyl, p-terphenyl, dibutyl phthalate, dimethyl glycol phthalate, dioctyl phthalate, triphenyl phosphate, methylnapthhalene, benzophenone, chlorinated paraffin, polypropyrene, polystyrene, dilauryl thiodipropionate, 3,5-dinitrosalicyclic acid and various fluoro hydrocarbons.

Examples of the charge transporting materials used in the electrophotographic light-sensitive materials shown in FIGS. 1-3 include the triphenylamine derivatives disclosed in U.S. Pat. Nos. 3,567,450 and 3,767,393; West German Patent Publication (DAS) No. 1,110,518; the polyarylalkane derivatives disclosed in U.S. Pat. Nos. 3,542,544, 3,542,547 and 4,127,412, etc.; the pyrazoline derivatives disclosed in U.S. Pat. Nos. 4,030,923 and 3,824,099; and the hydrazone derivatives disclosed in U.S. Pat. No. 3,717,462; Japanese Patent Application (OPI) No. 59,143/'79 (U.S. Pat. No. 4,150,987); U.S. Pat. No. 338,388, Japanese Patent Application Nos. 52,064/'80; 46,760/'80; 85,495/'80; U.S. patent application Ser. No. 276,745. These charge transporting materials may be used alone or as a mixture of two or more.

In this invention the light-sensitive wave length region can be controlled by using two or more compounds having (thio)barbituric acid residues having different light-sensitive wave length regions but the light-sensitive wave length region can be also controlled by using a known dye sensitizer together with the compound having a (thio)barbituric acid residue.

In addition, in the light-sensitive material prepared as described above, if necessary, an adhesive layer or a barrier layer may be formed between the conductive support and the light-sensitive layer. The materials used for the layer, include polyamide, nitrocellulose and aluminum oxide. The thickness of the layer is preferably less than 1 μm.

The light-sensitive material of this invention has a very high sensitivity, can be produced easily, and is excellent in durability. Also, the electrophotographic light-sensitive material of this invention is desirable because the wave length selectivity required when applying the light-sensitive material to a laser beam printer or an indication element is very high. In accordance with other uses of the light-sensitive of this invention, a printing plate (lithographic or relief printing plate) having high resolving power, high durability, and high sensitivity can be obtained by image exposing the light-sensitive material and after forming a toner image, etching the image.

The invention will now be explained more practically by the following examples but the invention is not limited to these examples. In addition, all "parts" is the examples are by weight.

EXAMPLE 1

In 130 parts of dichloromethane were dissolved 2 parts of the hydrazone compound having the following structural formula as a charge transporting material and 5 parts of polycarbonate of bisphenol A.

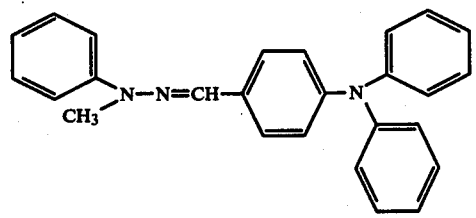

Then, 1 part of Compound (1) having thiobarbituric acid residue was dissolved in the solution of the charge transferring material to provide a coating composition for an electrophotographic light-sensitive layer. The coating position was coated on a conductive transparent support (of 100 μm in thickness), i.e., a polyethylene terephthalate support having a vapor-deposited layer of indium oxide (having a surface resistance of $10^3$ Ω) using a wire wound rod and dried to provide a light-sensitive material having a single layer-type electrophotographic light-sensitive layer of about 7 μm in thickness.

The light-sensitive material was positively charged by corona discharging of +5 KV using an electrostatic copying paper test machine (SP-428 type, made by Kawaguchi Denki Seisakusho K.K.), then the surface thereof was irradiated with light using a tungsten lamp of 3000° K. at a surface illuminance of 10 lux, and when the time required for decaying to half the initial surface potential was measured. The half decay light exposure amount $E_{50}$ was 63 lux.sec.

EXAMPLES 2-12

By following the same procedure as in Example 1 except that compounds having (thio)barbituric acid residues shown in following Table 1 were used in place of the charge generating material used in Example 1, single layer-type electrophotographic light-sensitive materials were prepared and the $E_{50}$ was measured on each sample. The results obtained are shown in Table 1.

TABLE 1

| Example | Compound* | Amount of the compound (part) | $E_{50}$ (lux.sec.) |
|---|---|---|---|
| 2 | (3) | 0.20 | 351 |
| 3 | (5) | 0.15 | 137 |
| 4 | (6) | 0.05 | 107 |
| 5 | (9) | 0.20 | 88 |
| 6 | (10) | 0.30 | 54 |
| 7 | (12) | 0.20 | 506 |
| 8 | (13) | 0.20 | 49 |
| 9 | (14) | 0.10 | 186 |
| 10 | (16) | 0.15 | 112 |
| 11 | (18) | 0.15 | 135 |
| 12 | (20) | 0.20 | 61 |

*Compound having barbituric acid residue.

EXAMPLE 13

On a sand-blasted aluminum plate of 100 μm in thickness was vapor-deposited Compound (1) having thiobarturic acid residue for 15 minutes at $2\times10^{-5}$ Torr and at a vapor-depositing temperature of 300° C. to form a charge generating layer of 0.5 μm in thickness.

Then, 5 parts of a charge transporting material, 4,4'-bis(diethylamino)-2,2'-dimethyltriphenylmethane and 4 parts of polycarbonate of bisphenol A were dissolved in 100 parts of dichloromethane. The solution was coated on the foregoing charge generating layer by a rotary coating method and dried to provide an electrophotographic light-sensitive material having a lamination-type electrophotographic light-sensitive layer of 7 μm in thickness.

When the sensitivity was measured as in Example 1, $E_{50}$ was 47.6 lux.sec.

EXAMPLE 14

| | |
|---|---|
| Hydrazone compound (Example 1) | 0.4 part |
| Copolymer of benzyl methacrylate and methacrylic acid 30° C. ([n] methylethylketone :0.12 methacrylic acid 32.9 mole %) | 1.0 part |
| Compound (13) having thiobarbituric acid residue | 0.04 part |

These components were dissolved in 8 parts of methylene chloride.

The solution was coated on a sand-blasted aluminum plate of 0.25 mm in thickness and dried to provide an electrophotographic light-sensitive printing plate having an electrophotographic light-sensitive layer of 6 mm in dry thickness.

The sample was charged by corona discharging of +6 KV in the dark so that the surface potential of the light-sensitive layer became about +600 volts and then when the sample was exposed to a tungsten lamp of a color temperature of 2854° K. at a surface illuminance of 30 lux, the half decay light exposure amount was 32 lux.sec.

Then, after charging the same in the dark at a surface potential of about +400 volts, the sample was image-exposed while contacting a transparent positive at the surface thereof. The sample was then immersed in a liquid developer containing toner prepared by adding 5 g of finely dispersed polymethyl methacrylate (toner) and 0.01 g of soybean oil lecithin to 1 liter of Isoper H (a petroleum oil solvent, made by Esso Standard Co.) to provide a sharp positive toner image.

Furthermore, the toner image was fixed by heating to 100° C. for 30 sec. The printing plate was immersed in a solution of 70 g of sodium metasilicate hydrate dissolved in a mixture of 140 ml of glycerol, 550 ml of ethylene glycol, and 150 ml of ethanol and by lightly brushing the surface with running water, the electrophotographic light-sensitive layer was removed at the areas carrying no toner.

Also, the electrostatic latent image was subjected to magnetic brush development using a toner for Xerox 3500 (made by Fuji Xerox Co.) in place of liquid development and then fixed by heating to 80° C. for 30 sec. Then, by removing the light-sensitive layer at the areas carrying no toner with an alkali solution, a printing plate was also obtained.

When printing was performed using the printing plate by means of a Hamada Star 600CD Offset Printer, very sharp 50,000 prints having no stains could be obtained.

While the invention has been described in detail and with reference to specific embodiments thereof, it will be apparent to one skilled in the art that various changes and modifications can be made therein without departing from the spirit and scope thereof.

What is claimed is:

1. A photoconductive composition containing a charge transporting material and a compound having a barbituric acid residue or a thiobarbituric acid residue represented by a general formula selected from the group of formulae consisting of (I) to (IV);

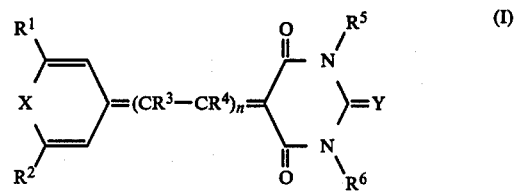

(I)

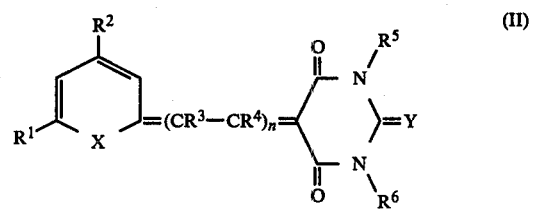

(II)

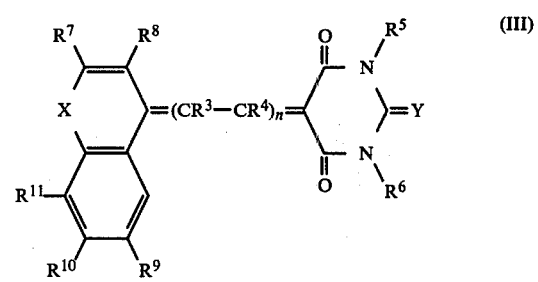

(III)

-continued

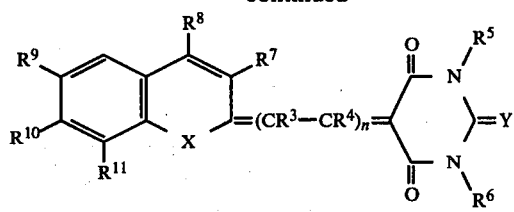

wherein;
(i) n represents 0, 1 or 2,
(ii) X and Y, which may be the same or different, each represents an oxygen atom or a sulfur atom,
(iii) $R^1$ and $R^2$, which may be the same or different, each represents a hydrogen, an alkyl group having 1–4 carbon atoms, or a phenyl group; these groups may have a substituent,
(iv) $R^3$ and $R^4$, which may be the same or different, each represents a hydrogen atom, an alkyl group, an aralkyl group, or an aryl group,
(v) $R^5$ and $R^6$, which may be the same or different, each represents a hydrogen atom, an alkyl group, an aralkyl group, or a phenyl group; these groups may have a substituent,
(vi) $R^7$ and $R^8$, which may be the same or different, each represents a hydrogen atom, an alkyl group having 1–4 carbon atoms, an unsubstituted or substituted phenyl group, and
(vii) $R^9$, $R^{10}$, and $R^{11}$, which may be the same or different, each represents a hydrogen atom, an alkyl group having 1–4 carbon atoms, a hydroxy group, an alkoxy group having 1–2 carbon atoms, an unsubstituted or substituted phenyl group, a nitro group, or a halogen atom.

2. A photoconductive composition containing a compound having a barbituric acid residue or a thiobarbituric acid residue represented by a general formula selected from the group of general formulae consisting of (I) to (IV);

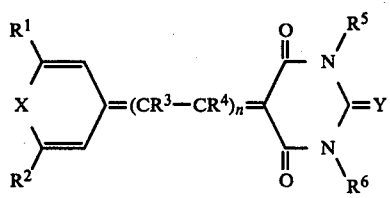

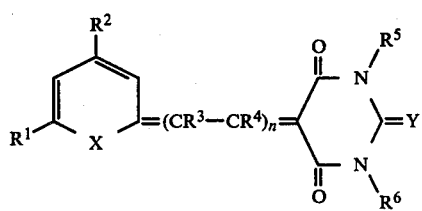

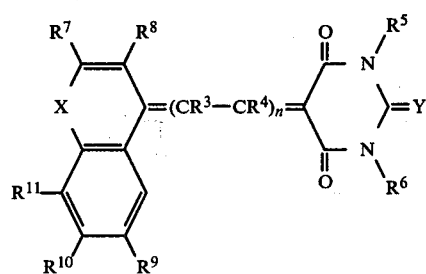

-continued

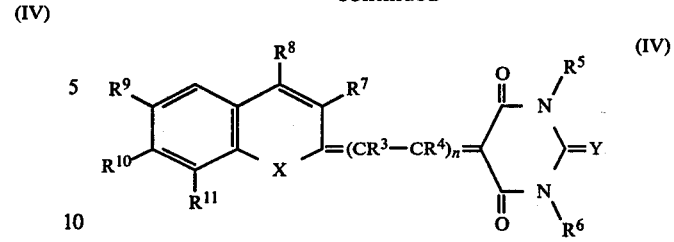

wherein;
(i) n represents 0, 1 or 2,
(ii) X and Y, which may be the same or different, each represents an oxygen atom or a sulfur atom,
(iii) $R^1$ and $R^2$, which may be the same or different, each represents a hydrogen, an alkyl group having 1–4 carbon atoms, or a phenyl group; these groups may have a substituent,
(iv) $R^3$ and $R^4$, which may be the same or different, each represents a hydrogen atom, an alkyl group, an aralkyl group, or an aryl group,
(v) $R^5$ and $R^6$, which may be the same or different, each represents a hydrogen atom, an alkyl group, an aralkyl group, or a phenyl group; these groups may have a substituent,
(vi) $R^7$ and $R^8$, which may be the same or different, each represents a hydrogen atom, an alkyl group having 1–4 carbon atoms, an unsubstituted or substituted phenyl group, and
(vii) $R^9$, $R^{10}$, and $R^{11}$, which may be the same or different, each represents a hydrogen atom, an alkyl group having 1–4 carbon atoms, a hydroxy group, an alkoxy group having 1–2 carbon atoms, an unsubstituted or substituted phenyl group, a nitro group, or a halogen atom.

3. An electrophotographic light-sensitive material, comprising an electrophotographic light-sensitive layer comprised of a charge generating material and a charge transporting material, characterized in that said charge generating material is comprised of a compound having a barbituric acid residue or a thiobarbituric acid residue represented by a general formula selected from the group of general formulae consisting of (I) to (IV);

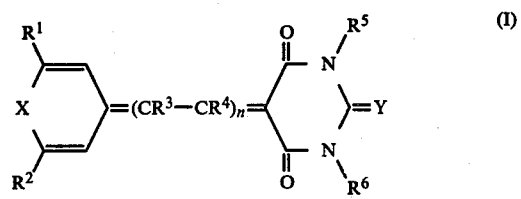

-continued

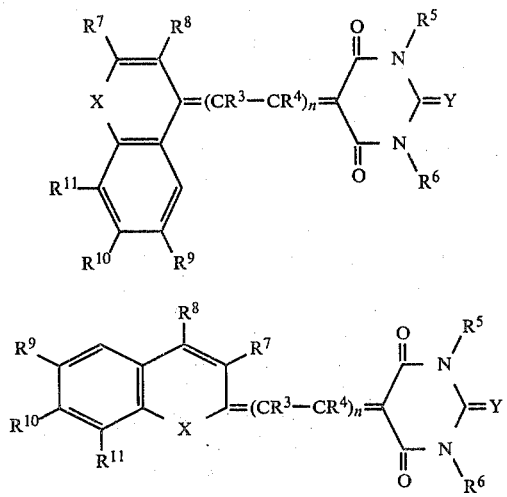

wherein;
(i) n represents 0, 1, or 2,
(ii) X and Y, which may be the same or different, each represents an oxygen atom or a sulfur atom,
(iii) $R^1$ and $R^2$, which may be the same or different, each represents a hydrogen atom, an alkyl group having 1-4 carbon atoms, or a phenyl group; these groups may have a substituent,
(iv) $R^3$ and $R^4$, which may be the same or different, each represents a hydrogen atom, an alkyl group, an aralkyl group, or an aryl group,
(v) $R^5$ and $R^6$, which may be the same or different, each represents a hydrogen atom, an alkyl group, an aralkyl group, or a phenyl group; these groups may have a substituent,
(vi) $R^7$ and $R^8$, which may be the same or different, each represents a hydrogen atom, an alkyl group having 1-4 carbon atoms, an unsubstituted or substituted phenyl group, or an unsubstituted or substituted naphthyl group, and
(vii) $R^9$, $R^{10}$, and $R^{11}$, which may be the same or different, each represents a hydrogen atom, an alkyl group having 1-4 carbon atoms, a hydroxy group, an alkoxy group having 1-2 carbon atoms, an unsubstituted or substituted phenyl group, a nitro group, or a halogen atom.

4. An electrophotographic light-sensitive material, comprising:
a support base having a conductive surface;
an electrophotographic light-sensitive layer comprised of a barbituric acid residue or a thiobarbituric acid residue as a charge generating material dispersed in a charge transfering medium comprised of a charge transporting material and a binder, wherein the barbituric acid residue or the thiobarbituric acid residue is represented by a general formula selected from the group of general formulae consisting of (I) to (IV):

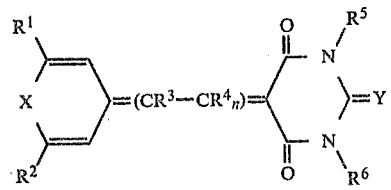

-continued

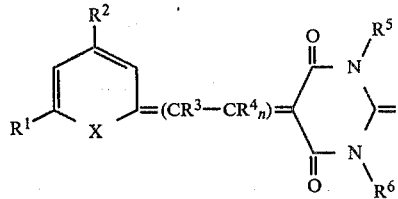

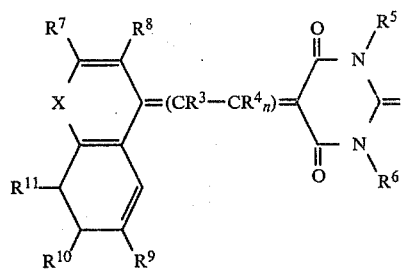

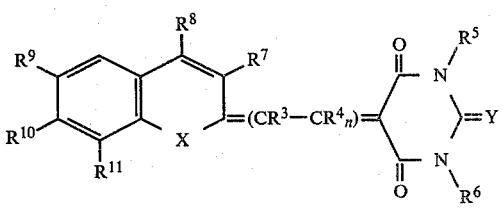

wherein;
(i) n represents 0, 1, or 2,
(ii) X and Y, which may be the same or different, each represents an oxygen atom or a sulfur atom,
(iii) $R^1$ and $R^2$, which may be the same or different, each represents a hydrogen atom, an alkyl group having 1-4 carbon atoms, or a phenyl group; these groups may have a substituent,
(iv) $R^3$ and $R^4$, which may be the same or different, each represents a hydrogen atom, an alkyl group, an aralkyl group, or an aryl group,
(v) $R^5$ and $R^6$, which may be the same or different, each represents a hydrogen atom, an alkyl group, an aralkyl group, or a phenyl group; said groups may have a substituent,
(vi) $R^7$ and $R^8$, which may be the same or different, each represents a hydrogen atom, an alkyl group having 1-4 carbon atom, an unsubstituted or substituted phenyl group, or an unsubstituted or substituted naphthyl group, and
(vii) $R^9$, $R^{10}$, and $R^{11}$, which may be the same or different, each represents a hydrogen atom, an alkyl group having 1-4 carbon atoms, a hydroxy group, an alkoxy group having 1-2 carbon atoms, an unsubstituted or substituted phenyl group, a nitro group, or a halogen atom.

5. An electrophotographic light-sensitive material comprising:
a support base having a conductive surface; and
an electrophotographic light-sensitive charge transfering layer comprised of a charge transporting material; and
a charge generating layer comprised of a barbituric acid residue or thiobarbituric acid residue represented by a general formula selected from the group of general formulae consisting of (I) to (IV):

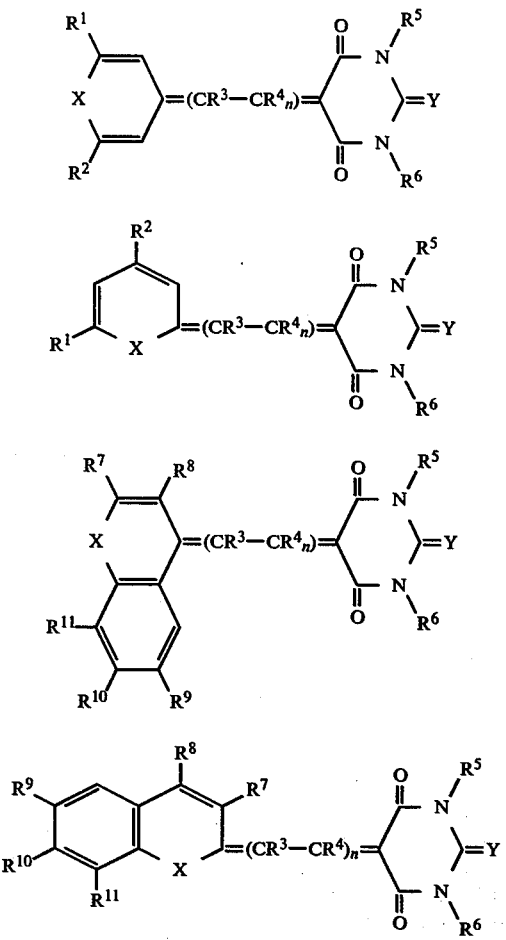

wherein;
(i) n represents 0, 1, or 2,
(ii) X and Y, which may be the same or different, each represents an oxygen atom or a sulfur atom,
(iii) $R^1$ and $R^2$, which may be the same or different, each represents a hydrogen atom, an alkyl group having 1-4 carbon atoms, or a phenyl group; these groups may have a substituent,
(iv) $R^3$ and $R^4$, which may be the same or different, each represents a hydrogen atom, an alkyl group, an aralkyl group, or an aryl group,
(v) $R^5$ and $R^6$, which may be the same or different, each represents a hydrogen atom, an alkyl group, an aralkyl group, or a phenyl group; said groups may have a substituent,
(vi) $R^7$ and $R^8$, which may be the same or different, each represents a hydrogen atom, an alkyl group having 1-4 carbon atoms, an unsubstituted or substituted phenyl group, or an unsubstituted or substituted naphthyl group, and
(vii) $R^9$, $R^{10}$, and $R^{11}$, which may be the same or different, each represents a hydrogen atom, an alkyl group having 1-4 carbon atoms, a hydroxy group, an alkoxy group having 1-2 carbon atoms, an unsubstituted or substituted phenyl group, a nitro group, or a halogen atom.

6. An electrophotographic light-sensitive material as claimed in claim 5, wherein the electrophotographic light sensitive layer has a thickness within a range of 3 to 50 μm.

7. An electrophotographic light-sensitive material as claimed in claim 5, wherein the charge generating layer has a thickness of 5 μm or less.

8. An electrophotographic light-sensitive material as claimed in claim 5, wherein the charge transfering layer has a thickness of 3 to 50 μm.

9. An electrophotographic light-sensitive material as claimed in claim 4, wherein the charge transporting material is present in an amount of 10 to 150% by weight based on the weight of the binder.

10. An electrophotographic light-sensitive material as claimed in claim 4, wherein the compound having the barbituric acid residue or the thiobarbituric acid residue is present in an amount of 1 to 150% by weight based on the weight of the binder.

11. An electrophotographic light-sensitive material as claimed in claim 5, wherein the charge transporting material in the charge transfering layer is present in an amount of 10 to 150% by weight.

* * * * *